United States Patent
Wilsher et al.

(10) Patent No.: US 10,047,235 B2
(45) Date of Patent: Aug. 14, 2018

(54) ENCODING LIQUID INK WITH A DEVICE SPECIFIC BIOMARKER

(71) Applicant: Xerox Corporation, Norwalk, CT (US)

(72) Inventors: Michael John Wilsher, Letchworth (GB); Jeremy Brook Lewis, London (GB)

(73) Assignee: Xerox Corporation, Norwalk, CT (US)

( * ) Notice: Subject to any disclaimer, the term of this patent is extended or adjusted under 35 U.S.C. 154(b) by 289 days.

(21) Appl. No.: 14/962,548

(22) Filed: Dec. 8, 2015

(65) Prior Publication Data
US 2017/0158897 A1 Jun. 8, 2017

(51) Int. Cl.
| | |
|---|---|
| *C09D 11/38* | (2014.01) |
| *C09D 11/50* | (2014.01) |
| *G01N 33/32* | (2006.01) |
| *B41J 2/175* | (2006.01) |
| *C09D 5/22* | (2006.01) |

(52) U.S. Cl.
CPC ............. *C09D 11/38* (2013.01); *B41J 2/175* (2013.01); *C09D 5/22* (2013.01); *G01N 33/32* (2013.01)

(58) Field of Classification Search
CPC .......... C09D 11/38; C09D 11/50; G01N 33/32
USPC .......... 106/31.13, 31.14, 31.15, 31.32, 31.43, 106/31.47, 31.64, 31.75, 31.76, 31.77
See application file for complete search history.

(56) References Cited

U.S. PATENT DOCUMENTS

| | | | | |
|---|---|---|---|---|
| 5,135,569 A | * | 8/1992 | Mathias ................ | C09D 11/50 106/31.15 |
| 5,139,812 A | * | 8/1992 | Lebacq ................ | B82Y 10/00 118/201 |
| 5,388,158 A | * | 2/1995 | Berson ................ | G07F 7/08 380/30 |
| 5,451,505 A | * | 9/1995 | Dollinger ............. | C06B 23/008 435/6.11 |
| 6,030,657 A | * | 2/2000 | Butland ............... | B41M 3/144 106/31.32 |

(Continued)

FOREIGN PATENT DOCUMENTS

| | | | |
|---|---|---|---|
| EP | 0938416 | | 4/2001 |
| JP | 2006/169341 | * | 6/2006 |
| WO | WO 87/06383 A | * | 10/1987 |

OTHER PUBLICATIONS

Jenkins, et al., "Glossary of Basic Terms in Polymer Science", Pur & Appl. Chem., Vo.. 68. No. 12, pp. 2287-2311, 1996.

*Primary Examiner* — Helene Klemanski
(74) *Attorney, Agent, or Firm* — Philip E. Blair; Fleit Gibbons Gutman Bongini & Bianco P.L.

(57) ABSTRACT

What is disclosed is a method for encoding liquid ink with a biomarker which can be traced back to a specific inkjet printer. In one embodiment, an aqueous solution containing a biomarker is combined with a volume of liquid ink. The biomarker comprises a nucleic acid. An ordering of nucleobases forming that nucleic acid has a code sequence. In one embodiment hereof, the nucleic acid is constructed using a code sequence which contains, at least in part, the device specific serial number of the inkjet printer. The encoded liquid ink is added to an inkjet printer and the code sequence encoded in that ink is associated with that particular inkjet printer. The inkjet printer is then used to deposit the encoded ink onto a media substrate. In other embodiments, a fluorescent marker is also added with the volume of liquid ink such that the ink fluoresces under an ultraviolet light.

20 Claims, 2 Drawing Sheets

(56) References Cited

U.S. PATENT DOCUMENTS

| | | | |
|---|---|---|---|
| 6,582,138 B1* | 6/2003 | Meunier | G06K 19/06028 235/487 |
| 6,616,964 B1* | 9/2003 | Hampp | C09B 61/00 106/31.32 |
| 6,706,314 B2* | 3/2004 | Butland | G09F 3/00 106/31.32 |
| 7,314,216 B2* | 1/2008 | Meunier | G06K 1/121 270/1.02 |
| 7,982,918 B2* | 7/2011 | Wilsher | H04N 1/32133 358/3.28 |
| 8,596,526 B2 | 12/2013 | Cleary et al. | |
| 2005/0045063 A1* | 3/2005 | Niggemann | C09D 11/50 106/31.43 |
| 2007/0172429 A1* | 7/2007 | Gao | G01N 33/58 424/10.2 |
| 2009/0042191 A1* | 2/2009 | Hayward | C09D 11/38 435/6.11 |
| 2010/0184154 A1 | 7/2010 | Miyoshi et al. | |
| 2013/0221277 A1* | 8/2013 | Ma | C09D 11/30 106/31.13 |
| 2015/0307728 A1* | 10/2015 | Omenetto | C09D 11/38 106/31.13 |

\* cited by examiner

ENCODING LIQUID INK WITH A DEVICE SPECIFIC BIOMARKER

TECHNICAL FIELD

The present invention is directed to methods for encoding liquid ink with a biomarker which can be traced back to a particular inkjet printer.

BACKGROUND

For security reasons, it is desirable to be able to authenticate a first generation document and further to be able to trace an original document back to a particular printer.

BRIEF SUMMARY

What is disclosed is a method for encoding liquid ink with a biomarker which can be traced back to a specific inkjet printer. In one embodiment, an aqueous solution containing a biomarker is combined with a volume of liquid ink. The biomarker comprises a nucleic acid. An ordering of nucleobases forming that nucleic acid has a code sequence. In one embodiment, the nucleic acid is constructed using a code sequence which contains, at least in part, the serial number of the inkjet printer. The encoded liquid ink is added to an inkjet printer and the code sequence encoded in that ink is associated with that particular inkjet printer. The inkjet printer is then used to deposit the encoded ink onto a media substrate. In other embodiments, a fluorescent marker is also added with the liquid ink such that the ink fluoresces under an ultraviolet light thereby providing a visual indication that the printed media has been printed with encoded liquid ink. Features and advantages of the present invention will become apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings.

DETAILED DESCRIPTION

What is disclosed is a method for encoding liquid ink with a biomarker which can be traced back to a particular inkjet printer.

An "aqueous solution" means a solution in which water ($H_2O$) is the solvent. The aqueous solution hereof contains a nucleic acid.

A "nucleic acid sequence" or simply "nucleic acid" is a macromolecule produced by biosynthesis, gene sequencing, or enzymatic synthesis. Although nucleic acids are naturally occurring in biological cellular structures, they can be designed to have a given sequence over a given length. Moreover, the sequence can be repeated over and over again in the nucleic acid. A given sequence can be replicated using, for example, oligonucleotide primers and a polymerase. Other methods for replicating a given nucleic acid sequence are well known in the genetic engineering arts. A nucleic acid sequence is made from building blocks of nucleotides.

"Nucleotides" are molecules comprising at least a nucleobase (also called a nitrogenous base), a five-carbon sugar (either 2-deoxyribose in the case of DNA or ribose in the case of RNA), and a phosphate group. Without the phosphate group, the nucleobase and sugar combination is called a nucleoside. Nucleobases are referred to as base pairs. At least one nucleobase is a derivative of a heterocyclic compound containing a metal ion.

"Base pairs" are either natural or unnatural. Natural base pairs are formed with any two of: Adenine (A), Cytosine (C), Guanine (G), or Uracil (U). Uracil and Thymine are identical except that Uracil lacks a 5' methyl group. An unnatural base pair (UBP), as used herein, is one which is not naturally occurring. The ordering of the base pairs forms a code sequence.

Figure 1:
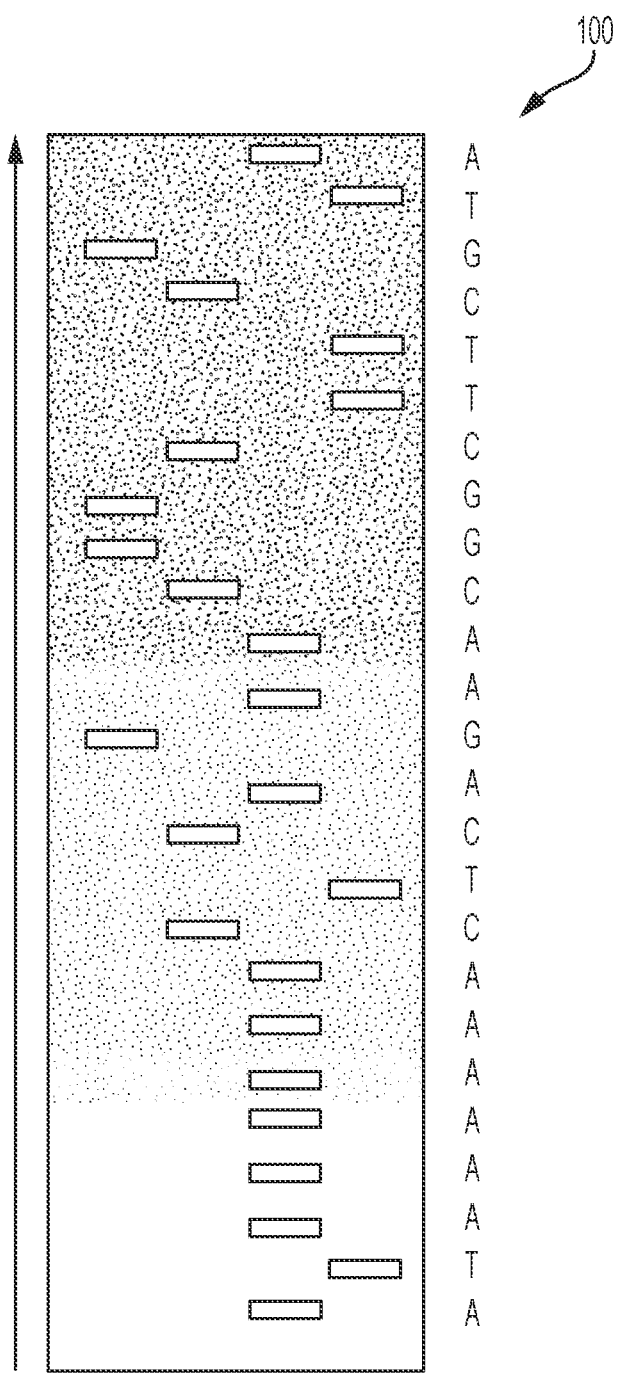
FIG. 1 shows an example code sequence obtained as a result of having decoded a nucleic acid using a sequencer.

A "code sequence", or simply "sequence", visually explains the ordering of the base pairs of a given nucleic acid which may or may not be unique. FIG. 1 shows an example sequence at 100 obtained as a result of having decoded a nucleic acid using a process of electrophoresis. The sequence can be alphabetic, numeric, alphanumeric, or symbolic. The sequence can be any length. The sequence can be given as a binary sequence of 1's and 0's, or a series of geometric symbols. The coding sequence will depend on the methodology employed to decode the nucleic acid. In DNA sequences comprising a double-stranded pattern, by convention, the top strand is written from the 5' end to the 3' end and the bottom strand is written from the 3' to the 5'. Nucleic acids can be decoded using a gene sequencer. In one embodiment hereof, the nucleic acid is constructed using a code sequence which contains, at least in part, the serial number of the inkjet printer.

A "gene sequencer" or simply "sequencer" is a highly sophisticated scientific instrument used to decode the ordering of the base pairs. The decoded ordering is reported as a string of numbers, characters, symbols, etc., depending on the design of the instrument. Some sequencers are considered optical instruments as they analyze light signals originating from fluorochromes attached to the nucleotides. Sequencers are commercially available in various streams of commerce by different vendors such as, for example, Hoffmann LaRoche, Illumina, Thermo Fisher Scientific, and Pacific Biosciences of California.

"Mixing" means combining and may involve stirring or shaking to achieve a desired uniformity. In one embodiment, the mixing involves replacing a volume of liquid ink with a volume of aqueous solution such that a total concentration of water in the volume of liquid ink remains substantially unchanged. In another embodiment, mixing involves adding an amount of aqueous solution to the liquid ink such that it does not exceed 1% by volume of liquid ink. A fluorescent marker may be added either directly to the liquid ink or to the aqueous solution such that the ink printed on the media substrate fluoresces under ultraviolet light.

"Associating" a code sequence with an inkjet printer means to use the encoded volume of liquid ink in a manner such that, upon decoding, the printed media can effectively be traced to a particular printer. In one example, the associating comprises placing a sticker with the ink's code sequence onto the inkjet printer. This list is exemplary and is not to be view as limiting. Other forms of "mixing" as well as other forms of "associating" are intended to fall within the scope of the appended claims.

Flow Diagram of One Embodiment

Figure 2:
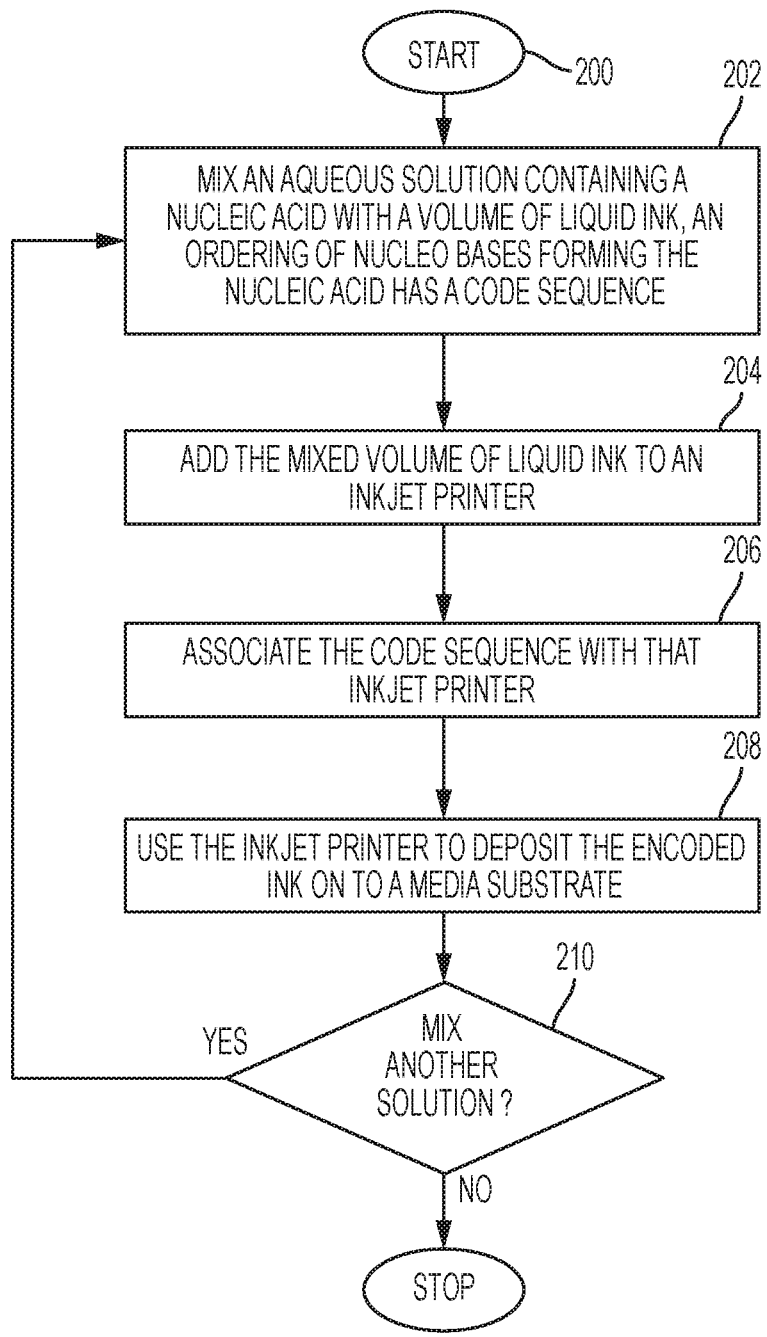
FIG. 2 is a flow diagram of one example embodiment of the present method for encoding liquid ink with a biomarker which can be traced back to a particular inkjet printer.

Reference is now being made to FIG. 2 which is a flow diagram of one embodiment of the present method for encoding liquid ink with a biomarker which can be traced to a particular inkjet printer. Flow processing begins at step 200 and immediately proceeds to step 202.

At step 202, mix an aqueous solution containing a nucleic acid with a volume of liquid ink, an ordering of pairs of nucleobases forming the nucleic acid has a code sequence.

One example of a code sequence is shown in FIG. 1. In one embodiment hereof, the nucleic acid is constructed using a code sequence which contains, at least in part, the serial number of the inkjet printer.

At step 204, add the mixed volume of liquid ink to an inkjet printer. This can be effectuated by, for example, installing the inkjet cartridge containing the encoded liquid ink into the inkjet printer.

At step 206, associate the code sequence with the inkjet printer (of step 204). This can be done by, for example, attaching a sticker containing the code sequence onto the inkjet printer, or by saving the code sequence to a software or hardware file or folder which, in turn, is associated with the serial number of the inkjet printer.

At step 208, use the inkjet printer to deposit the encoded ink onto a media substrate such as, for example, a sheet of xerographic paper.

At step 210, a determination is made whether to mix another aqueous solution to a volume of liquid ink. If so, then flow processing continues withrespect to step 202 wherein another aqueous solution is mixed with the same or a different volume of liquid ink. Flow processing repeats in a similar manner until no more aqueous solutions are desired to be mixed with another volume of liquid ink. Thereafter, in this embodiment, flow processing stops.

It should be understood that the flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims.

One or more aspects of the teachings herein are intended to be incorporated in an article of manufacture which may be shipped, sold, leased, or otherwise provided separately either alone or as part of a product suite or a service. The above-disclosed and other features, functions, or alternatives thereof, may be desirably combined into other different systems or applications. Presently unforeseen or unanticipated alternatives, modifications, variations, or improvements may become apparent and/or subsequently made by those skilled in this art which are also intended to be encompassed by the following claims.

What is claimed is:

1. A method for tracing a printed media back to a specific inkjet printer, the method comprising:
    replicating a nucleic acid containing ordered nucleobases, an ordering of said nucleobases comprising a code sequence associated with a specific inkjet printer;
    mixing, with a volume of liquid ink, an aqueous solution containing said nucleic acid sequence with a volume of liquid ink, said mixing being any of: replacing an amount of said liquid ink with said aqueous solution, and adding said aqueous solution to said liquid ink;
    adding said mixed volume of liquid ink to said specific inkjet printer;
    depositing, by said specific inkjet printer, said added mixed volume of liquid ink on to a media substrate to generate a printed media;
    using a sequencer to decode said ordered nucleobases mixed with said volume of liquid ink deposited on said printed media to obtain said code sequence; and
    using said obtained code sequence to identify said specific inkjet printer used to generate said printed media.

2. The method of claim 1, wherein mixing comprises replacing a volume of liquid ink with a similar volume of aqueous solution such that a total concentration of water in said liquid ink remains substantially unchanged.

3. The method of claim 1, wherein said given code sequence is alphabetic.

4. The method of claim 1, wherein said nucleobases are formed between any two of: Adenine (A), Cytosine (C), Guanine (G), Thymine (T), and Uracil (U).

5. The method of claim 1, wherein at least one nucleobase is an unnatural base pair (UBP).

6. The method of claim 1, wherein at least one nucleobase is a derivative of a heterocyclic compound containing a metal ion.

7. The method of claim 1, further comprising adding a fluorescent marker such that said liquid ink fluoresces under an ultraviolet light.

8. The method of claim 1, wherein said given code sequence is alphanumeric.

9. The method of claim 1, wherein said given code sequence is binary.

10. The method of claim 1, wherein said given code sequence is symbolic.

11. A liquid ink for an inkjet printer comprising:
    a volume of liquid ink; and
    an aqueous solution containing a nucleic acid, said nucleic acid having been replicated to contain ordered nucleobases, an ordering of said nucleobases comprising a code sequence associated with a specific inkjet printer, said association being any of: a sticker with said code sequence placed on to said specific inkjet printer, and a serial number of said specific inkjet printer, said aqueous solution being mixed with said volume of liquid ink, said mixing being any of: replacing an amount of said liquid ink with said aqueous solution, and adding said aqueous solution to said liquid ink, a sequencer being able to obtain said ordering of said nucleobases from said mixed volume of liquid ink thereby enabling a media substrate printed with said mixed volume of liquid ink to be traced back to said specific inkjet printer.

12. The liquid ink of claim 11, wherein said aqueous solution replaces a volume of liquid ink with a similar volume of aqueous solution such that a total concentration of water in said liquid ink remains substantially unchanged.

13. The liquid ink of claim 11, wherein said code sequence is alphabetic.

14. The liquid ink of claim 11, wherein said nucleobases are formed between any two of: Adenine (A), Cytosine (C), Guanine (G), Thymine (T), and Uracil (U).

15. The liquid ink of claim 11, wherein at least one nucleobase is an unnatural base pair (UBP).

16. The liquid ink of claim 11, further comprising adding a fluorescent marker such that said liquid ink fluoresces under an ultraviolet light.

17. The liquid ink of claim 11, wherein at least one nucleobase is a derivative of a heterocyclic compound containing a metal ion.

18. The liquid ink of claim 11, wherein said given code sequence is alphanumeric.

19. The liquid ink of claim 11, wherein said given code sequence is binary.

20. The liquid ink of claim 11, wherein said given code sequence is symbolic.

* * * * *